US008034374B2

(12) United States Patent
Takada et al.

(10) Patent No.: US 8,034,374 B2
(45) Date of Patent: *Oct. 11, 2011

(54) PATCH CONTAINING NONSTEROIDAL ANTI-INFLAMMATORY AND ANALGESIC AGENT

(75) Inventors: Yasunori Takada, Tosu (JP); Koji Tanaka, Tosu (JP); Kiyomi Tsuruda, Tosu (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 537 days.

This patent is subject to a terminal disclaimer.

(21) Appl. No.: 10/549,184

(22) PCT Filed: Mar. 18, 2004

(86) PCT No.: PCT/JP2004/003664
§ 371 (c)(1),
(2), (4) Date: Dec. 19, 2005

(87) PCT Pub. No.: WO2004/082672
PCT Pub. Date: Sep. 30, 2004

(65) Prior Publication Data
US 2006/0172002 A1 Aug. 3, 2006

(30) Foreign Application Priority Data
Mar. 18, 2003 (JP) .................. 2003-074117

(51) Int. Cl.
*A61K 31/192* (2006.01)
*A61K 9/70* (2006.01)
(52) U.S. Cl. ........................................... 424/449
(58) Field of Classification Search .......... None
See application file for complete search history.

(56) References Cited

U.S. PATENT DOCUMENTS

| 4,695,465 | A | * | 9/1987 | Kigasawa et al. | 424/449 |
| 5,120,545 | A | * | 6/1992 | Ledger et al. | 424/449 |
| 5,869,087 | A | * | 2/1999 | Hirano et al. | 424/449 |
| 5,914,322 | A | * | 6/1999 | Falk et al. | 514/54 |
| 5,945,125 | A | * | 8/1999 | Kim | 424/473 |
| 6,262,121 | B1 | * | 7/2001 | Kawaji et al. | 514/567 |
| 6,451,339 | B2 | * | 9/2002 | Patel et al. | 424/451 |
| 6,455,067 | B1 | * | 9/2002 | Woo et al. | 424/449 |
| 6,616,941 | B1 | * | 9/2003 | Seo et al. | 424/450 |
| 2003/0149383 | A1 | | 8/2003 | Ikeura et al. | |
| 2004/0146548 | A1 | * | 7/2004 | Takada et al. | 424/449 |

FOREIGN PATENT DOCUMENTS

| CA | 2 380 128 A1 | 12/2001 |
| EP | 1 477 164 A1 | 11/2004 |
| JP | 10-182450 A | 7/1998 |
| JP | 2001-233769 A | 8/2001 |
| JP | 2001-302502 A | 10/2001 |
| JP | 2002-020274 A | 1/2002 |
| JP | 2002-193793 A | 7/2002 |
| JP | 2002-226366 A | 8/2002 |
| KR | 10-0191062 B1 | 6/1999 |
| WO | WO 96/08245 A1 | 3/1996 |
| WO | WO 01/78690 A1 | 10/2001 |

OTHER PUBLICATIONS

Machine Translation of JP 2001-302502 A from JPO AIPN online translation.*
The Office Action issued on Dec. 27, 2010, in a counterpart European patent application (No. 04721660.1), six pages total.
Office Action issued on Oct. 22, 2010, in a counterpart Canadian patent application; 3 pages.
The Office Action issued on Nov. 5, 2010, in a counterpart Korean patent application (No. 10-2005-7017273), with English translation of information regarding issuance and cited documents, five pages total.

* cited by examiner

*Primary Examiner* — Sharmila G. Landau
*Assistant Examiner* — Rachael Welter
(74) *Attorney, Agent, or Firm* — The Nath Law Group; Susanne M. Hopkins; Ari G. Zytcer

(57) ABSTRACT

An adhesive patch containing a non-steroidal anti-inflammatory agent, comprising a support and an adhesive layer laminated on this support, wherein the adhesive layer contains a non-steroidal anti-inflammatory agent having a carboxyl group or its salt, and polyethylene glycol having an average molecular weight of 1000 or more.

5 Claims, No Drawings

PATCH CONTAINING NONSTEROIDAL ANTI-INFLAMMATORY AND ANALGESIC AGENT

This Application is the National Phase of International Application No. PCT/JP2004/003664 filed Mar. 18, 2004, which designated the U.S. and was not published under PCT Article 21(2) in English, and this application claims, via the aforesaid International Application, the foreign priority benefit of and claims the priority from Japanese Application No. 2003-074117, filed Mar. 18, 2003, the complete disclosures of which are incorporated herein by reference.

TECHNICAL FIELD

This invention relates to an adhesive patch containing a non-steroidal anti-inflammatory agent.

BACKGROUND ART

Many transdermal adhesive patches are known which provide a non-steroidal anti-inflammatory agent via skin absorption, however they have a problem in that the storage stability of non-steroidal anti-inflammatory agents, and in particular non-steroidal anti-inflammatory agents containing a carboxyl group or their salts, was low.

For this purpose, in International Publication No. WO96/08245, an adhesive patch is described wherein a non-steroidal anti-inflammatory agent having a carboxylic acid group in the molecule is blended with a base material comprising a styrene-isoprene-styrene block copolymer and polyisobutylene as a base polymer, L-menthol as a solvent, a rosine ester derivative as a tackifier, liquid paraffin as a plasticizer, and fatty acid metal salt as an esterification inhibitor which prevents esterification of the above non-steroidal anti-inflammatory agent with L-menthol, is proposed. Also, in Japanese Unexamined Patent Publication No. 2002-226366, an adhesive patch wherein a metal oxide is blended as an esterification inhibitor which prevents esterification of a non-steroidal anti-inflammatory agent having a carboxylic acid group in the molecule with L-menthol, is proposed. Further, in Japanese Unexamined Patent Publication No. 2002-193793, it is proposed to stabilize a non-steroidal anti-inflammatory agent having a carboxylic acid group in the molecule by dissolving it in a glycerin and a glycol having 3-30 carbon atoms.

DISCLOSURE OF THE INVENTION

However, the inventors discovered that, even in the case of the prior art adhesive patches described in the aforesaid references, if they contained a non-steroidal anti-inflammatory agent comprising a carboxyl group or its salts having a low storage stability as the pharmacological ingredient, the storage stability was still poor under stringent conditions such as a temperature of 40° C. or more.

It is therefore an object of the present invention, which was conceived in view of the aforesaid problems, to provide an adhesive patch containing a non-steroidal anti-inflammatory agent having a carboxyl group or its salts as a pharmacological ingredient wherein the long-term storage stability is excellent even under stringent conditions such as a temperature of 40° C. or more.

The inventors, as a result of intensive studies aimed at achieving the above objective, discovered that by containing a polyethylene glycol having an average molecular weight of 1000 or more in an adhesive patch containing the non-steroidal anti-inflammatory agent having a carboxyl group or it salt, not only was a solubility of the non-steroidal anti-inflammatory agent improved, but the long-term storage stability under stringent conditions was remarkably enhanced, and thereby arrived at the present invention.

The present invention therefore provides an adhesive patch containing a support and an adhesive layer laminated on the support, wherein a non-steroidal anti-inflammatory agent having a carboxyl group or it salt and polyethylene glycol having an average molecular weight of 1000 or more are contained in the adhesive layer.

The adhesive patch containing a non-steroidal anti-inflammatory agent of the invention has excellent long-term storage stability even under stringent conditions such as a high temperature of 40° C. or more. Also, the release properties of the non-steroidal anti-inflammatory agent are excellent. The reason for obtaining these effects is not totally clear, but it may be that due to containing polyethylene glycol in the adhesive layer and making the molecular weight of the glycol 1000 or more, the non-steroidal anti-inflammatory agent can be satisfactorily dispersed in the adhesive layer, and its solubility can be adjusted to be within a suitable range. Also, polyethylene glycol having an average molecular weight of 1000 or more, has less hydroxyl groups per unit weight than polyethylene glycol of low molecular weight (average molecular weight about 200-600), but in addition, the mobility of molecules in the adhesive layer is low, which probably stabilizes the non-steroidal anti-inflammatory agent.

The adhesive patch of the invention preferably further contains a fatty acid metal salt in the adhesive layer. This fatty acid metal salt is more preferably at least one moiety selected from among a group comprising zinc undecylenate, zinc stearate, aluminum stearate, calcium stearate, magnesium stearate, sodium stearate, zinc palmitate, zinc myristate, magnesium myristate, zinc laurate and sodium laurate, and among these, zinc stearate is most preferred.

In the adhesive patch of the invention, the non-steroidal anti-inflammatory agent is preferably at least one moiety selected from among a group comprising ketoprofen, diclofenac, flurbiprofen, ketorolac, felbinac or their pharmacological acceptable salts, and more preferably at least one moiety selected from among a group comprising diclofenac and its pharmacologically acceptable salts.

It is particularly preferred that the adhesive patch of the invention contains 1-25 mass % of at least one moiety selected from among a group comprising diclofenac and its pharmacologically acceptable salts, 1-6 mass % of polyethylene glycol having an average molecular weight of 1000 or more, and 1-6 mass % of the aforesaid fatty acid metal salt.

BEST MODE FOR CARRYING OUT THE INVENTION

Hereafter, some suitable aspects of the adhesive patch containing the non-steroidal anti-inflammatory agent of the invention will be described. The adhesive patch of the invention comprises a support, and an adhesive layer (pressure-sensitive adhesive layer) laminated on the support, and may further have a laminated, detachable film which can be peeled off when the patch is used. The adhesive layer of the adhesive patch of the invention contains a non-steroidal anti-inflammatory agent having a carboxyl group or its salt, and polyethylene glycol having an average molecular weight of 1000 or more.

First, the adhesive layer in the adhesive patch containing the non-steroidal anti-inflammatory agent of the invention will be described. The adhesive layer of the invention, in addition to an adhesive base material, contains the non-steroidal anti-inflammatory agent having a carboxyl group or it salt, and polyethylene glycol having an average molecular weight of 1000 or more.

The adhesive base material according to the invention may for example be styrene-isoprene-styrene block copolymer, styrene-butadiene-styrene block copolymer, styrene-isoprene rubber, styrene-butadiene rubber, polyisoprene, polyisobutylene, polybutadiene rubber, silicone rubber, an acrylic polymer (at least two copolymers selected from among butyl acrylate, 2-ethylhexyl acrylate, vinyl acetate, methacrylate, hydroxyethyl acrylate, glycidyl methacrylate, methoxyethyl acrylate and acrylic acid), natural rubber and polyurethane rubber. Among these, styrene-isoprene-styrene block copolymer and polyisobutylene are preferred from the viewpoint of cohesiveness, weatherability, anti-aging properties and reagent resistance, and a mixture of styrene-isoprene-styrene block copolymer and polyisobutylene is particularly preferred.

This styrene-isoprene-styrene block copolymer may for example be Califlex TR-1107, TR-1111, TR-1112, TR-1117 (product name, Shell Chemicals Ltd.), Quintac 3530, 3421, 3570C (product name, Nippon Zeon Ltd.), JSR SIS-5229, 5002 (product name, Japan Synthetic Rubber Ltd.), Kraton D-KX401CS, D-1107CU (product name, Shell Chemicals Ltd.) and Solprene 428 (product name, Philips Petroleum Ltd.), whereof one may be used alone or two or more may be used in combination. The blending proportion of the styrene-isoprene-styrene block copolymer is preferably 5-40 mass % and more preferably 10-35 mass % of the total adhesive layer (adhesive material). If this blending proportion is less than the aforesaid lower limit, the cohesiveness and shape retention properties of the base material decrease, whereas on the other hand if it exceeds the aforesaid upper limit, the cohesiveness increases, while adhesive force and working efficiency tend to decrease.

The polyisobutylene may for example be Oppanol B-3, B-10, B-15, B-50, B-100, B-200 (product name, BASF Ltd.), Vistanex LM-MS, LM-MH, MML-80, LLM-100, LLM-120, LLM-140 (product name, Exxon Ltd.) or Tetrax 3T, 4T, 5T, 6T (product name, Nippon Petrochemicals Ltd.), whereof one may be used alone, or two or more may be used in combination. The blending proportion of the polyisobutylene is preferably 1-25 mass % and more preferably 2-20 mass % of the total adhesive layer (adhesive material). If this blending proportion is less than the aforesaid upper limit, the adhesive force of the base material decreases, whereas on the other hand if it exceeds the aforesaid upper limit, shape retention properties of the base material during long-term storage decrease.

The non-steroidal anti-inflammatory agent having a carboxyl group or its salt is blended as a pharmacological ingredient together with the aforesaid adhesive base material in the adhesive layer according to the present invention. This anti-inflammatory agent comprises an anti-inflammatory agent having a carboxyl group (e.g., indmethacin, ketoprofen, flurbiprofen, felbinac, diclofenac, loxoprofen, ketorolac), and an anti-inflammatory agent wherein the hydrogen atom of the carboxyl group is substituted by a pharmacologically acceptable salt. Among these, ketoprofen, diclofenac, flurbiprofen, ketorolac, felbinac and their pharmacologically acceptable salts are preferred, and ketoprofen, diclofenac and their pharmacologically acceptable salts are particularly preferred. Compounds which form pharmacologically acceptable salts of the aforesaid medications include alkali metals, alkaline earth metals and ammonium compounds, specifically sodium, potassium, calcium, magnesium, ammonia, dimethylamine, diethylamine, trimethylamine, tetramethylammonium, monoethanolamine, diethanolamine and triethanolamine.

The blending proportion of the non-steroidal anti-inflammatory agent in the adhesive layer according to the invention is not particularly limited, but about 0.5-30 mass % of the total adhesive layer is common, and if diclofenac or its pharmacologically acceptable salt (in particular, sodium diclofenac) is used, 1-25 mass % of the total adhesive layer is preferred. If the blending proportion of the anti-inflammatory agent is less than the aforesaid upper limit, a sufficient pharmacological action is not obtained, whereas on the other hand if the blending proportion exceeds the aforesaid upper limit, adverse effects such as skin irritation due to overdosage may occur, and it is also disadvantageous from the viewpoint of economic efficiency. One of these non-steroidal anti-inflammatory agents may be used, or two or more may be used in combination.

The adhesive layer according to the invention contains polyethylene glycol which acts as a solvent for the aforesaid non-steroidal anti-inflammatory agent having a carboxyl group or its salt. Whereas the polyethylene glycol used as a solvent and the prior art had an average molecular weight of about 200-600, the polyethylene glycol used in the present invention has an average molecular weight of 1000 or more and preferably 1500-20,000. If the average molecular weight of the polyethylene glycol is less than 1000, long-term storage stability under stringent storage conditions decreases. On the other hand, if the average molecular weight of the polyethylene glycol exceeds 20,000, affinity with the medication increases and release properties decrease. The enhancement of long-term storage stability due to the aforesaid polyethylene glycol is well manifested in the case of the aforesaid non-steroidal anti-inflammatory agent having a carboxyl group or its salt, and better manifested in the case of diclofenac or pharmacologically acceptable salts thereof (in particular, sodium diclofenac).

The blending proportion of the polyethylene glycol in the adhesive layer according to the invention is not particularly limited, but it is generally of the order of 0.5-20 mass % of the total adhesive layer, and if diclofenac or pharmacologically acceptable salts thereof (in particular, sodium diclofenac) are used as pharmacological ingredients, the blending proportion of these polyethylene glycols is preferably 1-6 mass % of the total adhesive layer. If the blending proportion of the polyethylene glycol is less than the aforesaid lower limit, solubility in the base material of the medication decreases and crystals easily separate out, whereas on the other hand if the blending proportion exceeds the aforesaid upper limit, polyethylene glycol is excessive which leads to decrease of adhesive force and transdermal absorption. One of these polyethylene glycols may be used alone, or two or more may be used in combination.

In addition to the aforesaid non-steroidal anti-inflammatory agent and polyethylene glycol, a fatty acid metal salt is preferably blended with the adhesive layer according to the invention. This fatty acid metal salt functions as a stabilizer, and by blending the fatty acid metal salt, the stability of the adhesive layer is further enhanced. This fatty acid metal salt is at least one moeity selected from among a group comprising zinc undecylenate, zinc stearate, aluminum stearate, calcium stearate, magnesium stearate, sodium stearate, zinc palmitate, zinc myristate, magnesium myristate, zinc laurate and sodium laurate, and among these, zinc stearate is most preferred. The stabilizer effect of the aforesaid fatty acid metal salt is well manifested in the case of the aforesaid non-steroidal anti-inflammatory agent having a carboxyl group or it salt, but it is more pronounced in the case of diclofenac or its pharmacologically acceptable salts (in particular, sodium diclofenac).

The blending proportion of the fatty acid metal salt in the adhesive layer according to the invention is not particularly limited, but is generally of the order of 0.5-10 mass % of the total adhesive layer, and if diclofenac or its pharmacologically acceptable salt (preferably sodium diclofenac) is used as the pharmacological ingredient, the blending proportion of the fatty acid metal salt (preferably zinc stearate) is preferably 1-6 mass % of the total adhesive layer. If the blending proportion of the fatty acid metal salt is less than the aforesaid lower limit, the stabilizing effect of the fatty acid metal salt is not fully realized and crystals easily form in the adhesive layer, whereas on the other hand if the blending proportion exceeds the aforesaid upper limit, adhesive properties are impaired due to decrease of cohesiveness of the adhesive. One of the aforesaid fatty acid metal salts may be used alone, or two or more may be used together.

In addition to the aforesaid ingredients, the adhesive layer according to the present invention preferably contains a rosin resin and/or petroleum resin as a tackifier. This rosin resin may for example be natural resin rosin, modified rosin, a rosin ester (rosin glycerin ester, rosin pentaerythrytol ester) or a hydrated rosin ester (hydrated rosin glycerin ester, hydrated rosin pentaerythrytol ester), among which hydrated rosin esters are preferred and hydrated rosin glycerin ester is particularly preferred from the viewpoint of skin irritation and anti-aging. This rosin resin may specifically be Ester Gum H (product name, Arakawa Chemical Industries Ltd.), Pine Crystal KE-100, KE-311 (product name, Arakawa Chemical Industries Ltd.), Foral 85, 105 (product name, Rika-Hercules Ltd.) and Staybelite Ester 7, 10 (product name, Rika-Hercules Ltd.). One of these may be used alone, or two or more may be used in combination.

The petroleum resin may be a C5 synthetic petroleum resin (at least two copolymers selected from among isoprene, cyclopentadiene, 1,3-pentadiene and 1-pentene; at least two copolymers selected from among 2-pentene and dicyclopentadiene; a resin having 1,3-pentadiene as its main ingredient), a C9 synthetic petroleum resin (at least two copolymers selected from among indene, styrene, methylindene and α-methylstyrene), and a dicyclopentadiene synthetic petroleum resin (copolymer of isoprene having dicyclopentadiene as its main ingredient and/or 1,3-pentadiene), but from the viewpoint of weatherability and compatibility of the adhesive base material, a C9 petroleum resin is preferred. From another viewpoint, the petroleum resin may also be an alicyclic petroleum resin (alicyclic hydrocarbon resin), alicyclic hydrated petroleum resin, aliphatic petroleum resin (aliphatic hydrocarbon resin), aliphatic hydrated petroleum resin or an aromatic petroleum resin. From the viewpoint of adhesive force, compatibility with the adhesive base material and anti-aging properties, an alicyclic petroleum resin or alicyclic hydrated petroleum resin is preferred, and an alicyclic hydrated petroleum resin is particularly preferred. This petroleum resin may specifically be Arkon P-70, Arkon P-90, Arkon P-100, Arkon P-115 and Arkon P125 (product name, Arakawa Chemical Industries Ltd.) or Escorez 8000 (product name, Esso Petrochemicals Ltd.). One or more of these may be used alone, or two or more may be used in combination.

The adhesive layer according to the invention, in addition to the rosin resin and/or petroleum resin, may further contain another type of tackifier (terpene resin, phenol resin or xylene resin).

In the adhesive layer according to the invention, the blending proportion of the aforesaid tackifier is preferably 15 mass %-50 mass %, but more preferably 20 mass %-45 mass %. If this blending proportion is less than the aforesaid lower limit, sufficient adhesive force which permits long-term application is difficult to obtain, whereas on the other hand if it exceeds the aforesaid upper limit, medication release properties decrease, there is pain when the patch is peeled off and skin rashes easily occur.

Also, in the case of an acid medication wherein the blended material is diclofenac or its pharmacologically acceptable salt, the adhesive layer preferably further contains an adduct salt of a basic substance (e.g., an acid adduct salt of a basic substance). The adduct salt of this basic substance is a compound obtained by the addition of another substance to the basic substance to form a salt. The basic substance is preferably a Lewis base, the other substance preferably being a substance such as an electron-deficient compound derived from an electron pair acceptor such as a Lewis acid or organohalogen compound. This adduct salt of the basic substance may specifically be a salt of an ammonium compound, preferably an acid adduct salt of ammonia such as ammonium chloride or an acid adduct salt of an amine such as diethylamine hydrochloride. When the adduct of the basic substance is added, the cation part undergoes ion exchange or forms a complex ionic substance with part or all of the cation part of the acid medication. As a result, the ion exchange product or complex ionic substance improves the transdermal absorption of the medication.

The blending proportion of the adduct salt of the basic substance in the adhesive layer according to the invention may be a sufficient amount to form ion pairs with the acid medication, and is generally preferably within the range of 0.5-10 times the number of moles of acid medication. One of the adduct salts of the basic substance may be used alone, or two or more may be used in combination.

The adhesive patch of the invention may further contain an organic acid in the adhesive layer. The organic acid may be an aliphatic (mono, di, tri) carboxylic acid (acetic acid, propionic acid, isobutyric acid, caproic acid, caprylic acid, lactic acid, maleic acid, pyruvic acid, oxalic acid, succinic acid, tartaric acid), aromatic carboxylic acid (phthalic acid, salicylic acid, benzoic acid, acetylsalicylic acid), alkyl sulfonic acid (methanesulfonic acid, -ethanesulfonic acid, propyl sulfonic acid, butane sulfonic acid, polyoxyethylene alkylether sulfonic acid), alkyl sulfonic acid derivative (N-2-hydroxyethyl piperidine-N'-2-ethanesulfonic acid) or cholic acid derivative (dehydrocholate). Among these, a monocarboxylic acid or alkylsulfonic acid is preferred, and acetic acid is particularly preferred. These organic acids may be used in the form of their salts, or a mixture of the organic acid with its salt may be used.

As for these organic acids and/or salts, considering the transdermal penetration and skin irritation, they are preferably blended within the range of 0.01-20 mass %, more preferably 0.1-15 mass % and still more preferably 0.1-10 mass % based on the mass of the total composition forming the adhesive layer. If this blending proportion is less than 0.01 mass %, the skin penetration of the medication is not sufficient, whereas if it exceeds 20 mass %, skin irritation easily occurs.

The adhesive patch of the invention preferably further contains an absorption enhancer in the adhesive layer. This absorption enhancer may be any compound known in the prior art to enhance skin absorption. Examples are as follows:
(1) a fatty acid, aliphatic alcohol, aliphatic amide or aliphatic ether having 6-20 carbon atoms (saturated or unsaturated, and cyclic, straight-chain or branched),
(2) an aromatic organic acid, aromatic alcohol, aromatic organic acid ester or ether, (3) a lactic acid ester, acetic acid ester, monoterpene compound, sesquiterpene compound, Azone, Azone derivative, glycerin fatty acid ester, propylene glycol fatty acid ester, sorbitan fatty acid ester (Span type), polysorbate type (Tween type), polyethylene glycol fatty acid ester, polyoxyethylene hardening castor-oil type (HCO type), polyoxyethylene alkylether, sucrose fatty acid ester or vegetable oil.

Specific examples are caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, diethanolamide laurate, myristyl myristate, octyl dodecyl myristate, cetyl palmitate, methyl salicylate, ethylene glycol salicylate, cinnamic acid, methylcinnamate, creosol, cetyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprylate, glycerin monocaprate, glycerin monolaurate, glycerin mono-oleate, sorbitan monolaurate, sucrose monolaurate, polysorbate 20, propylene glycol monolaurate, polyethylene glycol monolaurate, polyethylene glycol monostearate, polyoxyethylene oleyl ether, polyoxyethylene lauryl ether, HCO-60, pyrrothiodecane and olive oil. Among these, oleic acid, lauryl alcohol, myristyl alcohol, oleyl alcohol, isostearyl alcohol, diethanolamide laurate, L-menthol, glycerin monocaprylate, glycerin monocaprate, glycerin monooleate, sorbitan monolaurate, propylene glycol monolaurate, polyoxyethylene oleyl ether, polyoxyethylene lauryl ether and pyrrothiodecane are more preferred, and oleic acid, oleyl alcohol and L-menthol are particularly preferred. In the case of an acid medication wherein the blended material is diclofenac or its pharmacologically acceptable salt, the skin penetration of the medication tends to be more improved by use of oleic acid, oleyl alcohol or L-menthol as an absorption, and it is especially improved in the case of L-menthol.

Two or more of these absorption enhancers may be mixed together, a combination of oleic acid and L-menthol or a combination of oleyl alcohol and L-menthol being preferred. Using these combinations, the skin penetration of the medication is particularly enhanced. From the viewpoint of sufficient penetration as a adhesive patch, and skin irritation such as reddening or swelling, these absorption enhancers are preferably blended in the range of 0.01-20 mass %, more preferably 0.05-10 mass % and most preferably 0.1-5 mass % based on the total mass of the composition forming the adhesive layer.

The adhesive patch of the invention may further contain a plasticizer in the adhesive layer. This plasticizer may for example be liquid paraffin, petroleum oil (paraffin process oil, naphthene process oil, aromatic process oil), squalane, squalene, vegetable oil (olive oil, camellia oil, castor oil, tall oil, peanut oil), silicone oil, a dibasic acid ester (dibutyl phthalate, dioctyl phthalate), liquid rubber (polybutene, liquid isoprene rubber) or glycol salicylate. Among these, liquid paraffin and liquid polybutene are particularly preferred.

Two or more of these plasticizers may be used in admixture. The blending proportion of plasticizer based on the total composition forming the adhesive layer, to maintain sufficient penetration and sufficient cohesive force as an adhesive patch, is preferably within the range of 5-70 mass %, more preferably 10-60 mass % and still more preferably 10-50 mass %.

In addition, in the adhesive patch of the invention, an anti-oxidant, filler, crosslinking agent, antiseptic and ultraviolet absorbent may be further blended together with the adhesive layer as required. This anti-oxidant is preferably a tocopherol or ester derivative thereof, ascorbic acid, ascorbic acid stearic acid ester, nordihydroguaiaretic acid, dibutyl hydroxytoluene (BHT) or butylated hydroxyanisole. The filler is preferably calcium carbonate, magnesium carbonate, a silicate (for example, aluminum silicate or magnesium silicate), silicic acid, barium sulfate, calcium sulfate, calcium zincate, zinc oxide or titanium oxide. The crosslinking agent is preferably a thermosetting resin of an amino resin, phenol resin, epoxide resin, alkyd resin or unsaturated polyester, an isocyanate compound, block isocyanate compound, organic crosslinking agent or inorganic crosslinking agent such as a metal or metal compound. The antiseptic is preferably ethyl p-oxybenzoate, propyl p-oxybenzoate or butyl p-oxybenzoate. The ultraviolet absorption agent is preferably a p-aminobenzoic acid derivative, anthranilic acid derivative, salicylic acid derivative, coumarin derivative, amino acid compound, imidazoline derivative, pyrimidine derivative or dioxane derivative.

The blending proportion of the anti-oxidant, filler, crosslinking agent, antiseptic and ultraviolet absorbent is preferably within the range of 10 mass % or less, more preferably 5 mass % and still more preferably 2 mass % or less, based on the total mass of the composition forming the adhesive patch.

The thickness of the adhesive layer (not including the thickness of the support and peel-off coating) according to the invention prepared using the aforesaid ingredients, is preferably 50-300 μm, but more preferably 80-200 μm. If the thickness is less than 50 μm, it is more difficult to maintain tackiness and adhesive properties, whereas if the thickness exceeds 300 μn, cohesive force and mold retention decrease.

The support of the adhesive patch containing the non-steroidal anti-inflammatory of the invention preferably has no effect on the release of the medication, and an expandable or non-expandable support may be used. Supports which can be used in the present invention include a synthetic resin film, sheet, sheet-like porous body, sheet-like foam, cloth or non-woven fabric of polyethylene, polypropylene, polybutadiene, ethylene-vinyl acetate copolymer, polyvinyl chloride, polyester, nylon or polyurethane; paper; or laminates thereof.

Next, a method of manufacturing the adhesive patch containing the non-steroidal anti-inflammatory of the invention will be described. First, the ingredients forming the adhesive layer (except the medication) are heated and mixed together in respectively predetermined proportions in an inert atmosphere such as nitrogen, the medication is added, and stirred to obtain a uniform melt. An organic solvent such as hexane, toluene or ethyl acetate is then added so that the aforesaid ingredients and medication are in respectively predetermined proportions, and stirred to give a homogeneous solution.

Next, this solution is spread directly on a support by the usual method, covered by a peel-off material and cut to a desired shape. Alternatively, the solution may be spread on a peel-off material which is then placed on a support, the solution transferred to the support under pressure, and cut to a desired shape. Preferably, if a uniform solution can be obtained using an organic solvent, it may be coated on the support and dried in a drier to remove the organic solvent by evaporation, and then covered by the peel-off material. Alternatively, it may be coated on the peel-off material, dried in a drier to remove the organic solvent by evaporation, and transferred to the support under pressure.

This peel-off material may for example be a peel-off (e.g., silicone treated) paper, cellophane or synthetic resin film (polyethylene, polypropylene, polyester, polyvinyl chloride or polyvinylidene chloride).

This is only given as an example of the blending sequence of base material ingredients, medications and other additives in this manufacturing method, and the method of manufacturing the adhesive patch is not limited to this blending sequence.

EXAMPLES

Hereafter, the invention will be described referring to specific examples and comparative examples, but the invention is not to be construed as being limited in anyway thereby, various modifications being possible within the scope and spirit of the appended claims.

Example 1

The following ingredients were mixed with toluene to form a mixture, and this was stirred to form a homogeneous solution. Next, this solution was spread on a peel-off material (polyester film) so that the thickness after drying was 100 μm. The toluene was evaporated by drying, the residue was coated on a support (polyester cloth, thickness approximately 550 μm), and the adhesive layer was transferred to the support under pressure to obtain a adhesive patch containing a non-steroidal anti-inflammatory agent. The figures in the following ingredients refer to mass %.
(Formula)

| | |
|---|---|
| SIS | 10 |
| PIB | 15 |
| Liquid paraffin | 31 |
| Alicyclic petroleum resin | 30 |
| Ammonium chloride | 1 |
| Oleic acid | 2 |
| L-menthol | 2 |
| Polyethylene glycol | 2 |
| Zinc stearate | 4 |
| Sodium diclofenac | 3 |

The following materials were used for the above ingredients. SIS (styrene-isoprene-styrene block copolymer): Japan Synthetic Rubber Ltd., product name: SIS-5229;
PIB (polyisobutylene): BASF, product name: Oppanol B-200;
Liquid paraffin: Kaneda Ltd., product name: Hi-Call M-352;
Alicyclic petroleum resin: Arakawa Chemical Industries Ltd., product name: Arkon P-100;
Polyethylene glycol: Sanyo Chemical Industries Ltd., product name: Macrogol 1500, average molecular weight: 1300-1600.

Examples 2-3 and Comparative Examples 1-3

An adhesive patch containing a non-steroidal anti-inflammatory agent was obtained in an identical way to Example 1, except the following materials were used for polyethylene glycol.

Example 2

Sanyo Chemical Industries Ltd., product name: Macrogol 4000, average molecular weight: 2600-3800;

Example 3

Sanyo Chemical Industries Ltd., product name: Macrogol 6000, average molecular weight: 7300-9300;

Comparative Example 1

Sanyo Chemical Industries Ltd., product name: Macrogol 200, average molecular weight: 190-210;

Comparative Example 2

Sanyo Chemical Industries Ltd., product name: Macrogol 400, average molecular weight: 380-420;

Comparative Example 3

Sanyo Chemical Industries Ltd., product name: Macrogol 600, average molecular weight: 570-630.

Example 4

An adhesive patch containing a non-steroidal anti-inflammatory agent was obtained in an identical way to Example 1, except zinc stearate was not blended with the composition.

Test 1 (Pharmacological Stability Test Under Stringent Storage Conditions)

The pharmacological stability of the adhesive patch containing a non-steroidal anti-inflammatory agent according to Examples 1-3 and Comparative Examples 1-3, was evaluated as follows. The adhesive patch was stored at 40° C. for 2 months, 3 months and 6 months, and at 50° C. for 2 months and 3 months, the residual amount of medication (diclofenac) in the patch after storage was measured by liquid chromatography, and the residual medication (%) was computed. The test was repeated 3 times. TABLE 1 shows the average of the obtained results

TABLE 1

| | 40° C.-2 months storage | 40° C.-3 months storage | 40° C.-6 months storage | 50° C.-2 months storage | 50° C.-3 months storage |
|---|---|---|---|---|---|
| Example 1 | 99.2 | 98.5 | 97.5 | 97.3 | 96.0 |
| Example 2 | 98.9 | 98.8 | 98.2 | 98.0 | 96.8 |
| Example 3 | 99.0 | 99.0 | 98.2 | 98.1 | 97.2 |
| Comp. Ex. 1 | 94.0 | 93.2 | 88.1 | 89.3 | 84.8 |
| Comp. Ex. 2 | 95.2 | 94.7 | 90.2 | 90.2 | 85.3 |
| Comp. Ex. 3 | 96.1 | 95.3 | 90.3 | 90.5 | 86.0 |

As can be seen from the results in TABLE 1, it was found that the adhesive patch containing the non-steroidal anti-inflammatory agent of the invention using polyethylene glycol having an average molecular weight of 1000 or more (Examples 1-3), had a much improved long-term storage stability under stringent conditions than the adhesive patch containing the non-steroidal anti-inflammatory agent for which the average molecular weight did not satisfy this condition (Comparative Examples 1-3). Adhesive patches for which the residual medication was less than 90% were deemed unsatisfactory.

Test 2 (Observation of Presence or Absence of Crystals in Adhesive Layer)

The presence or absence of crystals in the adhesive layer of the adhesive patch containing a non-steroidal anti-inflammatory agent obtained in Examples 1 and 4, was evaluated by observation with a microscope. As a result, it was found that whereas no crystals at all were observed in the adhesive layer obtained in Example 1, there was a slight amount of crystallization in the adhesive layer obtained in Example 4.

INDUSTRIAL APPLICABILITY

As described above, according to this invention, by using the adhesive patch containing a non-steroidal anti-inflammatory agent having a carboxyl group or its salt as a pharmacological ingredient, an adhesive patch containing a non-steroidal anti-inflammatory agent having excellent long-term storage stability even under the stringent conditions of a high temperature of 40° C. or more, can be obtained.

The invention claimed is:

1. A storage stable adhesive patch comprising:
a support; and
an adhesive layer laminated on the support, the adhesive layer comprising
1-25% by mass of sodium diclofenac,
1-6% by mass of polyethylene glycol having an average molecular weight in an amount selected from the group consisting of 1300-1600, 2600-3800 and 7300-9300,
1-6% by mass of zinc stearate,
ammonium chloride present in the range of 0.5-10 times the number of moles of sodium diclofenac,
20-45% by mass of alicyclic petroleum resin,
10-35% by mass of styrene-isoprene-styrene block copolymer, and
2-20% by mass of polyisobutylene.

2. The adhesive patch according to claim 1, wherein the adhesive layer further comprises 0.1-5% by mass of L-menthol.

3. The adhesive patch according to claim 1, wherein the adhesive layer further comprises 0.1-10% by mass of oleic acid.

4. The adhesive patch according to claim 1, wherein the adhesive layer further comprises 0.1-5% by mass of L-menthol, and 0.1-10% by mass of oleic acid.

5. The adhesive patch according to claim 1, wherein the adhesive layer further comprises
0.1-5% by mass of L-menthol,
0.1-10% by mass of oleic acid, and
10-50% by mass of a plasticizer.

* * * * *